United States Patent [19]

Wiener et al.

[11] Patent Number: 5,042,489
[45] Date of Patent: * Aug. 27, 1991

[54] ULTRASONIC DENSITOMETER DEVICE AND METHOD

[75] Inventors: Scott A. Wiener, Horeb, Wis.; Phillip J. Rossman, Rochester, Minn.

[73] Assignee: Lunar Corporation, Madison, Wis.

[*] Notice: The portion of the term of this patent subsequent to Jun. 5, 2007 has been disclaimed.

[21] Appl. No.: 595,115

[22] Filed: Oct. 10, 1990

Related U.S. Application Data

[63] Continuation-in-part of Ser. No. 343,170, Apr. 25, 1989, which is a continuation-in-part of Ser. No. 193,295, May 11, 1988, Pat. No. 4,930,511.

[51] Int. Cl.$^5$ .............................................. A61B 8/00
[52] U.S. Cl. ........................... 128/661.03; 128/660.06; 73/597; 73/599
[58] Field of Search ................ 128/660.01, 660.06, 128/661.02, 661.03; 73/597, 599

[56] References Cited

U.S. PATENT DOCUMENTS

| | | |
|---|---|---|
| 2,939,130 | 4/1948 | Firestone . |
| 3,345,863 | 10/1967 | Henry et al. . |
| 3,477,422 | 11/1969 | Jurist, Jr. et al. . |
| 3,587,561 | 6/1971 | Fiedonis . |
| 3,648,685 | 3/1972 | Hepp et al. . |
| 3,664,180 | 5/1972 | McDonald et al. . |
| 3,713,329 | 1/1973 | Munger . |
| 3,782,177 | 11/1974 | Hoop . |
| 3,847,141 | 11/1924 | Hoop . |
| 4,048,986 | 9/1977 | Ott . |
| 4,056,970 | 11/1977 | Sollish . |
| 4,105,018 | 8/1978 | Greenleaf et al. . |
| 4,138,999 | 2/1979 | Eckhart et al. . |
| 4,217,912 | 8/1980 | Hubmann et al. . |
| 4,233,845 | 11/1980 | Pratt, Jr. . |
| 4,235,243 | 11/1980 | Saha . |
| 4,240,895 | 2/1991 | Lees . |
| 4,316,183 | 2/1982 | Palmer et al. . |
| 4,361,154 | 12/1983 | Pratt, Jr. . |
| 4,421,119 | 11/1984 | Pratt, Jr. . |
| 4,476,873 | 10/1984 | Sorenson et al. . |
| 4,522,068 | 6/1985 | Smith . |
| 4,530,360 | 7/1985 | Duarte . |
| 4,597,292 | 7/1986 | Fujii et al. . |
| 4,669,482 | 6/1987 | Ophir . |
| 4,774,959 | 10/1988 | Palmer et al. . |

FOREIGN PATENT DOCUMENTS

| | | |
|---|---|---|
| 2313420 | 2/1977 | France . |
| 123798 | 2/1959 | U.S.S.R. . |
| 219853 | 6/1968 | U.S.S.R. . |

OTHER PUBLICATIONS

C. M. Langton, S. B. Palmer; and R. W. Porter, "The Measurement of Blood band Ultrasonic Attenuation in Concellous Bone," Eng. Med., vol. 13; pp. 89-91 (1984).
S. Lees, "Sonic Properties of Mineralized Tissue," *Tissue Characterization With Ultrasound*, CRC Publication 2, pp. 207-226 (1986).
J. D. Craven, M. A. Constantini, M. A. Greenfield; and R. Stern, "Measurement of the Velocity of Ultrasound in Human Cortical Bone and Its Potential Clinical Importance," *Investigative Radiology*, vol. 8; pp. 72-77 (1973).

(List continued on next page.)

*Primary Examiner*—Kyle L. Howell
*Assistant Examiner*—Scott D. Akers
*Attorney, Agent, or Firm*—Quarles & Brady

[57] ABSTRACT

An ultrasound densitometer is disclosed in which ultrasonic transducers are located spaced apart in a water bath into which the heel of a person may be inserted. The transit time of an ultrasonic pulse through the water can be compared to the time for a similar pulse with a heel inserted. A novel clinical indicia for bone integrity value has been developed to provide a single numerical indication related both to the speed of sound travel in the member and the ultrasonic broadband attenuation in the member. The bone integrity value numeral based on measurements in the os calcis has been found to correlate well with conventional measurements of spinal bone mineral content.

10 Claims, 6 Drawing Sheets

OTHER PUBLICATIONS

C. Rich, E. Klink; R. Smith, B. Graham, and P. Ivanovich, "Sonic Measurement of Bone Bass," *Progress in Development of Methods in Bone Densitometry*, pp. 137–146 (NASA 1966).

M. Greenspan and C. E. Tschiegg, "Sing-Around Ultrasonic Velocimeter for Liquids," *The Review of Scientific Instruments*, vol. 28; No. 11, pp. 897–901 (1957).

W. Abendschein and G. W. Hyatt, "Ultrasonics and Selected Physical Properties of Bone," *Clinical Orthopedics and Related Research*, No. 69, pp. 294–301 (1970).

M. Gerlanc, D. Haddad, G. Hyatt; J. Langloh, and P. St. Hilaire, "Ultrasonic Study of Normal and Fractured Bone," *Clinical Orthopedics and Related Research*, pp. 175–180 (1975).

B. Martin and R. R. Haynes, "The Relationship Between the Speed of Sound and Stiffness of Bone," *Biomechanics Laboratories*, West Virginia University (1970).

J. M. Hoop and W. N. Clotfelter, "Ultrasonic Bone Density Measurements," Marshall Space Flight Center, The Fall Conference of the American Society for Non-Destructive Testing (1970).

K. H. Okumura, "Preventative Diagnosis of Breakdown," Massachusetts Institute of Technology (1978).

W. N. McDicken, *Diagnostic Ultrasonics*, pp. 35–61 (1976).

Lees, S. and C. Davidson, "The Role of Collagen in the Elastic Properties of Calcified Tissues," *C. Journal of Biomechanics*, vol. 10; No. 7 (1977), pp. 473–548.

Van Venrooij, G.; "Measurement of Ultrasound Velocity in Human Tissue," *Ultrasonics*, Oct. (1971); pp. 24–242.

Lang, S.; "Ultrasonic Method for Measuring Elastic Coefficients of Bone and Results on Fresh and Dried Bones," *IEEE Transactions on Bio-Medical Engineering*; vol. BMI-17, No. 2 (Apr. 1970), pp. 101–105.

Martin, B. and R. Haynes, "The Investigation of Bone's Substructure Using Megahertz Sound and a Porous Model," *ASME Publication* (Dec. 3, 1970).

Mayor, M. B. and S. A. Brown, "Ultrasonic Prediction of Delayed or Nonunion of Fractures," *Proceedings of the Fifth New England Bioengineering Conference* (Apr. 15, 1977), pp. 229–233.

Brown, S. A. and M. B. Mayor; "Ultrasonic Assessment of Early Callus Formation," *Biomedical Engineering*, vol. 11; No. 4 (Apr. 1976), pp. 124–128.

Yamada, H.; "Strength of Biological Materials," pp. 53–57 (1970).

Wells, P. N. T.; "Physical Principals of Ultrasonic Diagnosis," *Academic Press*, London (1969); pp. 1–27.

Mather, B. S.; "Comparison of Two Formulae in vivo Prediction of Strength of the Femur," *Aerospace Medicine*; vol. 38, No. 12 (Dec. 1967) pp. 1270–1272.

Anast, G. T.; Fields and Siegel; I. M., "Ultrasonic Technique for the Evaluation of Bone Fractures," pp. 157–159.

Shulkla, Leu, Tighe, Krutoff, Craven and Greenfield; "A Study of the Honogeneity of the Trabecular Bone Mineral Density in the Calcaneus," *Medical Phys.*, pp. 687–691; vol. 14, No. 4, Jul./Aug. 1987.

Katz and Yoon, "The Structure and Anisotropic Mechanical Properties of Bone," *IEEE Transactions on Biomedical Engineering*, pp. 878–884; vol. BME-31. No. 12, 12/Poll, Cooper and Cawley, "Broadband Ultrasonic Attenuation in the Os Calls and Single Photon Absorptiometry in the Distal Forearm: A Comparative Study," *Clin. Phys. Physiol. Meas.*, 1986, vol. 7, No. 4, 375–379.

Rossman, "Measurements of Ultrasonic Velocity and Attenuation in the Human OS Calcis and Their Relationships to Photon Absorptiometry Bone Mineral Measurements," MS Thesis, University of Wisconsin–Madison, 1987.

Holm and Jones, "Use Discrete Fourier Transforms to Simplify Signal Processing", *EDN*; p. 203, Apr. 28, 1983.

Pinkowitz, "Fast Fourier Transform Speeds Signal-to Noise Analysis for A/D Converters," *Digital Design*, p. 64, May 1986.

Palmer and Langton, "Ultrasonic Studies of the Os–Calcis,".

Hellhake, Rabin, Pratt Jr. and Seder, "A Computer Aided Diagnostic Ultrasound System for In Vivo Analysis of Bone Strength,".

ULTRASONIC DENSITOMETER DEVICE AND METHOD

CROSS-REFERENCE TO RELATED APPLICATION

This application is a continuation-in-part of Ser. No. 07/343,170 filed Apr. 25, 1989, which is a continuation-in-part of Ser. No. 07/193,295 filed May 11, 1988, now U.S. Pat. No. 4,930,511.

BACKGROUND OF THE INVENTION

1. Field of the Invention

The present invention relates to devices which are used for measuring the density of members, such as bones, and more particularly to devices which utilize ultrasonic acoustic signals to measure the physical properties and integrity of the members 2. Description of the Prior Art Various devices presently exist which may be used to measure the physical properties and integrity of a member such as a bone. Non-invasive density measuring devices can be used to determine cumulative internal damage caused by micro-crushing and micro-fracturing occurring in the bones of humans or animals such as race horses. Additionally, osteoporosis, or loss of bone mineralization, detection in humans and its cure or prevention are increasingly becoming areas of intense medical and biological interest. As the average age of the human population increases, a greater number of patients are developing complications due to rapid trabecular bone loss.

U.S. Pat. No. 3,847,141 to Hoop discloses a device for measuring the density of a bone structure, such as a finger bone or heel bone, to monitor the calcium content thereof. The device includes a pair of opposed spaced ultrasonic transducers which are held within a clamping device clamped on the bone being analyzed A pulse generator is coupled to one of the transducers to generate an ultrasonic soundwave which is directed through the bone to the other transducer. An electric circuit couples the signals from the receive transducer back to the pulse generator for retriggering the pulse generator in response to those signals. The pulses therefore are produced at a frequency proportional to the transit time that the ultrasonic wave takes to travel through the bone structure, which is directly proportional to the speed of the sound through the bone. The speed of sound through a bone has been found to be proportional to the density of the bone. Thus the frequency at which the pulse generator is retriggered is proportional to the density of the bone.

Another device and method for establishing, in vivo the strength of a bone is disclosed in U.S. Pat. Nos. 4,361,154 and 4,421,119 to Pratt, Jr. The device includes a launching transducer and a receiving transducer which are connected by a graduated vernier and which determine the speed of sound through the bone to determine its strength. The vernier is used to measure the total transit distance between the surfaces of the two transducers.

Lees (Lees, S. (1986) Sonic Properties of Mineralized Tissue, *Tissue Characterization With Ultrasound*, CRC publication 2, pp. 207-226) discusses various studies involving attenuation and speed of sound measurements in both cortical and spongy (cancellous or trabecular) bone. The results of these studies reveal a linear relationship between the wet sonic velocity and wet cortical density, and between the dry sonic velocity and the dry cortical density. The transit times of an acoustic signal through a bone member therefore are proportional to the bone density. Langton, et al. (Langton, C.M., Palmer, S.D., and Porter, S.W., (1984) The Measurement of Broad Band Ultrasonic Attenuation in Cancellous Bone, Eng. Med., 13, 89-91) published the results of a study of ultrasonic attenuation versus frequency in the os calcis (heel bone) that utilized through transmission techniques. These authors suggested that attenuation differences observed in different subjects were due to changes in the mineral content of the os calcis. They also suggested that low frequency ultrasonic attenuation may be a parameter useful in the diagnosis of osteoporosis or as a predictor of possible fracture risk.

SUMMARUY OF THE INVENTION

The present invention is summarized in that an ultrasound densitometer for measuring the physical properties and integrity of a member in vivo, includes: a transmit transducer from which acoustic signals having at least one specific frequency component are transmitted through the member and through a material with known acoustic properties; a receive transducer which receives the acoustic signals after they have been transmitted through the member; means connected to said transducers for determining a member transit time of the acoustic signals through the member and/or for determining an absolute attenuation of at least one individual specific frequency component of the acoustic signals through the member, and for determining a material transit time of the acoustic signals through the material and/or for determining an absolute attenuation of at least one corresponding individual specific frequency component of the acoustic signals through said material.

Alternatively, the transmit transducer may transmit acoustic signals through the member, and the receive transducer receive acoustic signals after they have been transmitted through the member, the densitometer including a microprocessor with a database of normal transit times; means for selecting one of said normal transit times; means for making a mathematical comparison of said member transit time to the selected normal transit time; and means for relating said mathematical comparison to the physical properties and integrity of said member. Each of the normal transit times in the database may be dependent upon the age, height, weight, race, or sex of the individual being tested, or on the distance between the transducers, or on the thickness or size of the member.

A primary object of the invention is to provide an ultrasound densitometer device and method for measuring the physical properties and integrity of a member in vivo by determining the transit time of ultrasonic acoustic signals through the member quickly, efficiently and easily.

A second object of the invention is to provide an ultrasound densitometer device and method for measuring the physical properties and integrity of a member in vivo by comparing the transit time of ultrasonic acoustic signals through the member with the transit time of the acoustic signals through a material with known acoustic properties.

An additional object of the invention is to provide an ultrasound densitometer device and method for measuring the physical properties and integrity of a member in vivo by determining the absolute attenuation of specific frequency components of ultrasound acoustic signals through the member.

A further object of the invention is to provide an ultrasound densitometer device and method for measuring the physical properties and integrity of the member in vivo by comparing the absolute attenuation of specific frequency components of ultrasound acoustic signals through the member with the absolute attenuation of corresponding frequency components of acoustic signals through a material of known acoustic properties.

Another object of the invention is to provide an ultrasound densitometer device and method of measuring the physical properties and integrity of a member in vivo by comparing the transit time of ultrasonic acoustic signals through the member with a selected normal transit time selected from a database of normal transit times which are dependent upon the age, height, weight, race, or sex of an individual being tested, and also upon the distance between the transducers or the size of the member.

Yet an additional object of the invention is to provide ultrasound densitometer device and method for measuring the physical properties and integrity of a bone member in vivo which can display the density of the member and a digital composite member waveform of the received acoustic signal on a digital display.

Yet an additional object of the invention is to provide an ultrasound densitometer device and method for measuring the physical properties and integrity of a member in vivo which device has a transmit and a receive transducer which can each include an array of a plurality of elements, whereby the acoustic signals received by one or more of the receive elements may be analyzed to determine a relative position with respect to the member of each of the acoustic signals received by the receive elements.

Other objects, features and advantages of the invention will be apparent from the following detailed description taken in conjunction with the accompanying drawings wherein a preferred embodiment of the invention has been selected for exemplification.

DESCRIPTION OF THE PREFERRED EMBODIMENT

Figure 1:
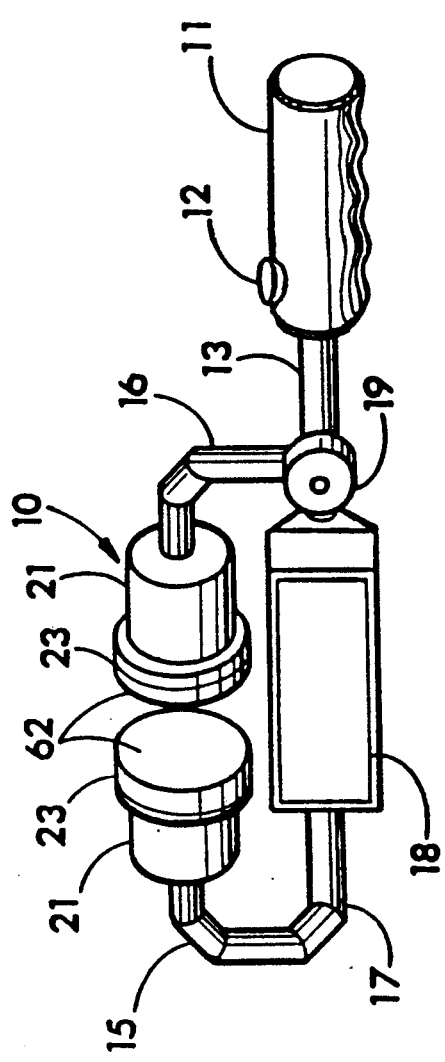
FIG. 1 is a perspective view of the ultrasound densitometer device constructed in accordance with the present invention.

Referring more particularly to the drawings, wherein like numbers refer to like parts, FIG. 1 shows a portable ultrasound densitometer 10 for measuring the physical properties and integrity of a member, such as a bone, in vivo. The densitometer 10 as shown in FIG. 1 includes a handle 11 with actuator button 12. Extending linearly from the handle 11 is a connection rod 13. The densitometer 10 also includes a fixed arm 15 and an adjustable arm 16. The fixed arm 15 preferably is formed continuously with the connection rod 13, and therefore is connected to an end 17 of the connection rod 13. The adjustable arm 16 is slidably mounted on the connection rod 13 between the handle 11 and a digital display 18 mounted on the rod 13. The knob 19 may be turned so as to be locked or unlocked to allow the adjustable arm 16 to be slid along the connection rod 13 so that the distance between the arms 15 and 16 may be adjusted.

Figure 3:
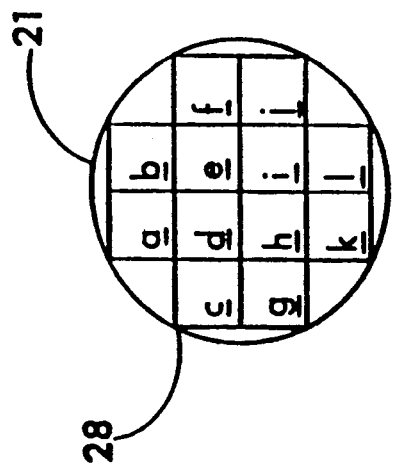
FIG. 3 is a front view of a transducer face from which acoustic signals are transmitted or by which acoustic signals are received, the face of the other transducer being the mirror image thereof
Figure 2:
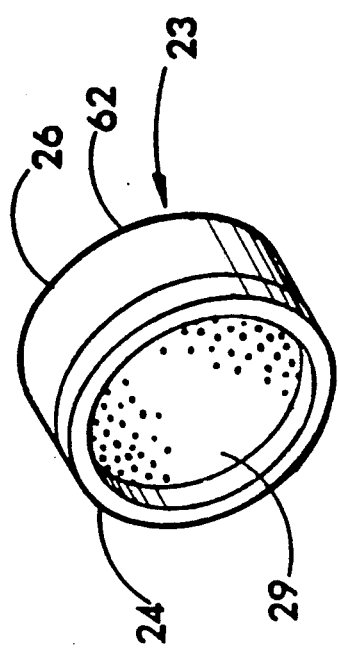
FIG. 2 is a perspective view of an acoustic coupler, two of which are shown in FIG. 1.

Connected at the end of the fixed arm 15 is a first (left) transducer 21 and at the end of the adjustable arm 16 is a second (right) transducer 21. As shown in FIGS. 1 and 2, each of the transducers 21 has mounted on it a respective compliant acoustic coupler 23 to acoustically couple the transducer to the object being tested. The acoustic coupler 23 includes a plastic ring 24 and attached pad 26 formed of urethane or other compliant material. FIG. 3 shows a face 28 of the first (left) transducer 21 which is normally hidden behind the compliant pad 26 of the acoustic coupler 23. The transducer face 28 normally abuts against the inner surface 29 of the pad 26 shown in FIG. 2. The transducer face 28 shown in FIG. 3 includes an array of twelve transducer elements labeled a-1. The second (right) transducer 21 includes a face 28 which is the mirror image of that shown in FIG. 3.

Figure 4:
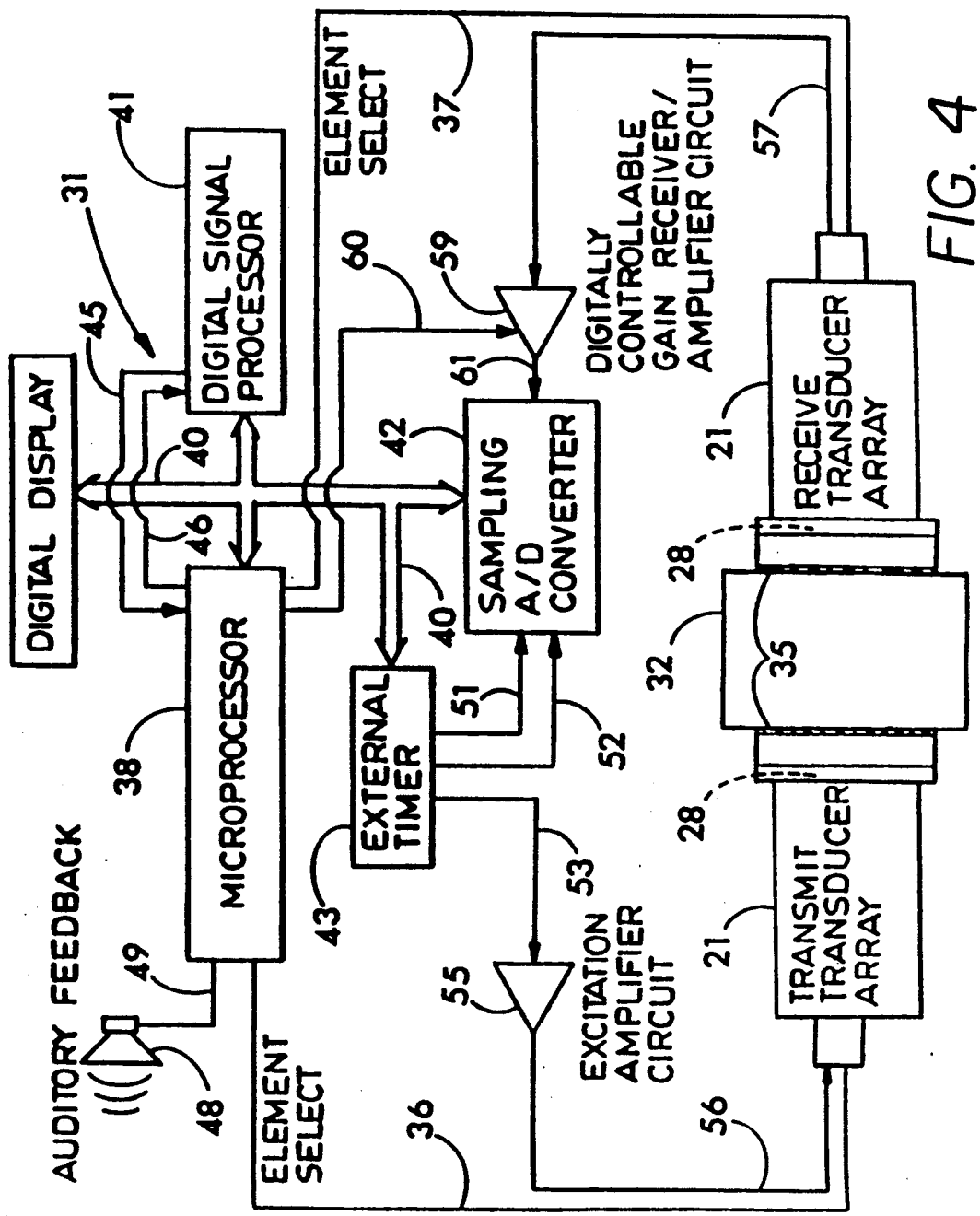
FIG. 4 is a schematic block diagram view of the circuitry of the ultrasound densitometer device constructed in accordance with the present invention.

FIG. 4 generally shows in schematic fashion the electronic circuitry 31 of the densitometer 10, which is physically contained in the housing of the digital display 18. An object 32 is placed between the two transducers 21 so that acoustic signals may be transmitted through the object. This object 32 represents a member, such as a bone, or some material with known acoustic properties such as distilled water or a neoprene reference block. As shown in the embodiment illustrated in FIG. 4, the leftmost transducer 21 is a transmit transducer and the rightmost transducer 21 a receive transducer. In fact though, either or both of the transducers 21 may be a transmit and/or receive transducer. The transmit and receive transducers 21 of the circuit of FIG. 4 are connected by element select signals 36 and 37 to a microprocessor 38. The microprocessor 38 is programmed to determine which one of the respective pairs of transducer elements a through 1 are to be transmitting and receiving at any one time. This selection is accomplished by the element select signal lines 36 and 37, which may be either multiple signal lines or a serial data line to transmit the needed selection data to the transducers 21. The microprocessor 38 is also connected by a data and address bus 40 to the digital display 18, a digital signal processor 41, a sampling analog to digital converter 42, and a set of external timers 43. The microprocessor 38 has "on board" electrically programmable non-volatile random access memory (NVRAM) and, perhaps as well, conventional RAM memory, and controls the operations of the densitometer 10. The digital signal processor 41 has "on board" read-only memory (ROM) and performs many of the mathematical functions carried out by the densitometer 10 under the control of the microprocessor 38. The digital signal processor 41 specifically includes the capability to perform discrete Fourier transforms, as is commercially available in integrated circuit form presently, so as to be able to convert received waveform signals from the time domain to the frequency domain. The microprocessor 38 and digital signal processor 41 are interconnected also by the control signals 45 and 46 so that the microprocessor 38 can maintain control over the operations of the digital signal processor 41 and receive status information back. Together the microprocessor 38 and the digital signal processor 41 control the electrical circuit 31 so that the densitometer 10 can carry out its operations, which will be discussed below. An auditory feedback mechanism 48, such as an audio speaker, can be connected to the microprocessor 38 through an output signal 49.

The external timer 43 provides a series of clock signals 51 and 52 to the A/D converter 42 to provide time information to the A/D converter 42 so that it will sample at timed intervals electrical signals which it receives ultimately from the transmit transducer, in accordance with the program in the microprocessor 38 and the digital signal processor 41. The external timer 43 also create a clock signal 53 to an excitation amplifier 55. Timed pulses are generated by the timer 43 and sent through the signal line 53 to the amplifier 55 to be amplified and directed to the transmit transducer 21 through the signal line 56. The transmit transducer 21 converts the amplified pulse into an acoustic signal which is transmitted through the object or material 32 to be received by the receive transducer 21 which converts the acoustic signal back to an electrical signal. The electrical signal is directed through output signal 57 to a receiver amplifier 59 which amplifies the electrical signal.

The excitation amplifier circuit 55 is preferably a digitally controllable circuit designed to create a pulsed output. The amplification of the pulse can be digitally controlled in steps from one to ninety-nine. In this way, the pulse can be repetitively increased in amplitude under digital control until a received pulse of appropriate amplitude is received at the receiver/amplifier circuit 59, where the gain is also digitally adjustable.

Connected to the receiver amplifier circuit 59 and integral therewith is a digitally controllable automatic gain control circuit which optimizes the sensitivity of the receive transducer 21 and the amplifier circuit 59 to received acoustic signals. The microprocessor 38 is connected to the amplifier circuit and automatic gain control 59 through signal line 60 to regulate the amplification of the amplifier circuit and gain control 59. The amplified electric signals are directed through lead 61 to the A/D converter 42 which samples those signals at timed intervals. The A/D converter 42 therefore in effect samples the received acoustic signals. As a series of substantially identical acoustic signals are received by the receive transducer 21, the A/D converter 42 progressively samples an incremental portion of each successive signal waveform. The microprocessor 38 is programmed so that those portions are combined to form a digital composite waveform which is nearly identical to a single waveform. This digitalized waveform may be displayed on the digital display 18, or processed for numerical analysis by the digital signal processor 41.

The densitometer constructed in accordance with FIGS. 1-4 can be operated in one or more of several distinct methods to measure the physical properties of the member, such as integrity or density. The different methods, as described in further detail below, depend both on the software programming the operation of the microprocessor 34 as well as the instructions given to the clinician as to how to use the densitometer. The different methods of use may all be programmed into a single unit, in which case a user-selectable switch may be provided to select the mode of operation, or a given densitometer could be constructed to be dedicated to a single mode of use. In any event, for the method of use of the densitometer to measure the physical properties of a member to be fully understood, it is first necessary to understand the internal operation of the densitometer itself.

In any of its methods of use, the densitometer is intended to be placed at some point in the process on the member whose properties are being measured This is done by placing the transducers 21 on the opposite sides of the member. To accomplish this, the knob 19 is loosened to allow the adjustable arm 16 to be moved so that the transducers 21 can be placed on opposite sides of the member, such as the heel of a human patient. The outside surfaces of the pads 26 can be placed against the heel of the subject with an ultrasound gel 35 or other coupling material placed between the pads 26 and subject 32 to allow for improved transmission of the acoustic signals between the member 32 and transducers 21. Once the transducers 21 are properly placed on the member, the knob 19 may be tightened to hold the adjustable arm 16 in place, with the transducers 21 in spaced relation to each other with the member 32 therebetween. The actuator button 12 may then be pressed so that acoustic signals will be transmitted through the member 32 to be received by the receive transducer 21. The electronic circuit of FIG. 4 receives the electrical signals from the receive transducer 21, and samples and processes these signals to obtain information on the physical properties and integrity of the member 32 in vivo. The microprocessor 38 is programmed to indicate on the digital display 18 when this information gathering process is complete. Alternatively, the information may be displayed on the digital display 18 when the information gathering process is completed. For example, the transit time of the acoustic signals through the member 32 could simply be displayed on the digital display 18.

Figure 5:
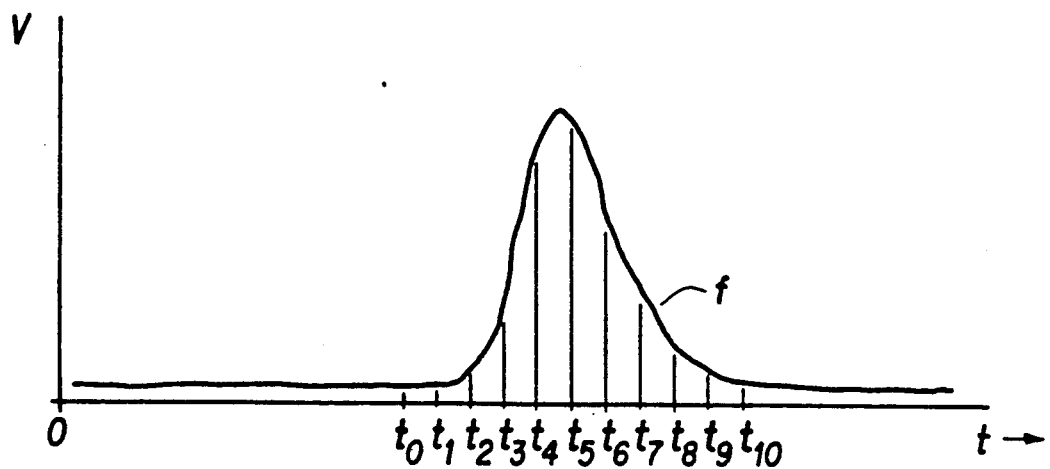
FIG. 5 illustrates the method of sampling a received waveform used by the circuit of FIG. 4.

Considering in detail the operation of the circuitry of FIG. 4, the general concept is that the circuitry is designed to create an ultrasonic pulse which travels from transmit transducer 21 through the subject 32 and is then received by the receive transducer 21. The circuitry is designed to both determine the transit time of the pulse through the member 32, to ascertain the attenuation of the pulse through the member 32, and to be able to reconstruct a digital representation of the waveform of the pulse after it has passed through the member 32, so that it may be analyzed to determine the attenuation at selected frequencies. To accomplish all of these objectives, the circuitry of FIG. 4 operates under the control of the microprocessor 38. The microprocessor 38 selectively selects, through the element select signal lines 36, a corresponding pair or a group of the elements a through 1 on the face of each of the transducers 21. The corresponding elements on each transducer are selected simultaneously while the remaining elements on the face of each transducer are inactive. With a given element, say for example element a selected, the microprocessor then causes the external timer 43 to emit a pulse on signal line 53 to the excitation amplifier circuit 55. The output of the excitation amplifier 55 travels along signal line 56 to element a of the transmit transducer 21, which thereupon emits the ultrasonic pulse. The corresponding element a on the receive transducer 21 receives the pulse and presents its output on the signal line 57 to the amplifier circuit 59. What is desired as an output of the A/D converter 42 is a digital representation of the analog waveform which is the output of the single transducer element which has been selected. Unfortunately, "real time" sampling A/D converters which can operate rapidly enough to sample a waveform at ultrasonic frequencies are relatively expensive. Therefore it is preferred that the A/D converter 42 be an "equivalent time" sampling A/D converter. By "equivalent time" sampling, it is meant that the A/D converter 42 samples the output of the transducer during a narrow time period after any given ultrasonic pulse. The general concept is illustrated in FIG. 5. The typical waveform of a single pulse received by the receive transducer 21 and imposed on the signal line 57 is indicated by a function "f". The same pulse is repetitively received as an excitation pulse is repetitively launched. The received pulse is sampled at a sequence of time periods labeled $t_0$–$t_{10}$. In other words, rather than trying to do a real-time analog to digital conversion of the signal f, the signal is sampled during individual fixed time periods $t_0$–$t_{10}$ after the transmit pulse is imposed, the analog value during each time period is converted to a digital function, and that data is stored. Thus the total analog wave form response can be recreated from the individual digital values created during each time period t, with the overall fidelity of the recreation of the wave form dependent on the number of time periods t which are sampled. The sampling is not accomplished during a single real time pulse from the receive transducer 21. Instead, a series of pulses are emitted from the transmit transducer 21. The external timer is constructed to provide signals to the sampling A/D converter 42 along signal lines 51 and 52 such that the analog value sampled at time period $t_0$ when the first pulse is applied to a given transducer element, then at time $t_1$ during the second pulse, time $t_2$ during the third pulse, etc. until all the time periods are sampled. Only after the complete waveform has been sampled for each element is the next element, i.e. element b, selected. The output from the A/D converter 42 is provided both to the microprocessor 38 and to the signal processor 41. Thus the digital output values representing the complex waveform f of FIG. 5 can be processed by the signal processor 41 after they are compiled for each transducer element. The waveform can then be analyzed for time delay or attenuation for any given frequency component with respect to the characteristic of the transmitted ultrasonic pulse. The process is then repeated for the other elements until all elements have been utilized to transmit a series of pulses sufficient to create digital data representing the waveform which was received at the receive transducer array 21. It is this data which may then be utilized in a variety of methods for determining the physical properties of the member, and determining on the manner in which the densitometer is being utilized, and the data being sought, the appropriate output can be provided from either the microprocessor 38 or the signal processor 41 through the digital display 18.

Because the ultrasonic pulsing and sampling can be performed so rapidly, at least in human terms, the process of creating a sampled ultrasonic received pulse can optionally be repeated several times to reduce noise by signal averaging. If this option is to be implemented, the process of repetitively launching ultrasonic pulses and sampling the received waveform as illustrated in FIG. 5 is repeated one or more times for each element in the array before proceeding to the next element. Then the sampled waveforms thus produced can be digitally averaged to produce a composite waveform that will have a lesser random noise component than any single sampled waveform. The number of repetitions necessary to sufficiently reduce noise can be determined by testing in a fashion known to one skilled in the art.

Having thus reviewed the internal operation of the densitometer of FIGS. 1-4, it is now possible to understand the methods of use of the densitometer to measure the physical properties of the member. The first method of use involves measuring transit time of an ultrasonic pulse through a subject and comparing that time to the time an ultrasonic pulse requires to travel an equal distance in a substance of known acoustic properties such as water. To use the densitometer in this procedure, the adjustable arm 16 is adjusted until the member of the subject, such as the heel, is clamped between the transducers 21. Then the knob 19 is tightened to fix the adjustable arm in place. The actuator button 12 is then pressed to initiate a pulse and measurement. Next the densitometer is removed from the subject while keeping the knob 19 tight so that the distance between the transducers 21 remains the same. The device 10 is then placed about or immersed in a standard material 32 with known acoustic properties, such as by immersion in a bath of distilled water. The actuator button 12 is pressed again so that acoustic signals are transmitted from the transmit transducer 21 through the material 32 to the receive transducer 21. While it is advantageous to utilize the whole array of elements a through 1 for the measurement of the member, it may only be necessary to use a single pair of elements for the measurement through the standard assuming only that the standard is homogeneous, unlike the member. The signal profiles received by the two measurements are then analyzed by the microprocessor 38 and the signal processor 41. This analysis can be directed both to the comparative time of transit of the pulse through the subject as compared to the standard and to the characteristics of the waveform in frequency response and attenuation through the subject as compared to the standard.

Thus in this method the densitometer may determine the physical properties and integrity of the member 32 by both or either of two forms of analysis. The densitometer may compare the transit time of the acoustic signals through the member with the transmit time of the acoustic signals through the material of known acoustic properties, and/or the device 10 may compare the attenuation as a function of frequency of the broadband acoustic signals through the member 32 with the absolute attenuation of corresponding specific frequency components of the acoustic signals through the material of known acoustic properties. The "attenuation" of an acoustic signal through a substance is the diminution of the ultrasonic waveform from the propagation through either the subject or the standard. The theory and experiments using both of these methods are presented and discussed in Rossman, P.J., Measurements of Ultrasonic Velocity and Attenuation In The Human Os Calcis and Their Relationships to Photon Absorptiometry Bone Mineral Measurements (1987) (a thesis submitted in partial fulfillment of the requirements for the degree of Master of Science at the University of Wisconsin-Madison). Tests have indicated that there exists a linear relationship between ultrasonic attenuation (measured in decibels) (db)) at specific frequencies, and those frequencies. The slope (dB/MHz) of the linear relationship, referred to as the broadband ultrasonic attenuation, is dependent upon the physical properties and integrity of the substance being tested. With a bone, the slope of the linear relationship would be dependent upon the bone mineral density. Thus broadband ultrasonic attenuation through a bone is a parameter directly related to the quality of the cancellous bone matrix.

The microprocessor 38 may therefore be programmed so that the device determines the physical properties and integrity of the member by comparing either relative transit times and/or relative broadband ultrasonic attenuation through the member and a material of known acoustic properties. When comparing the transit times, the microprocessor 38 may be programmed most simply so that the electronics, having received the acoustic signals after they have been transmitted through the member, determines the "member" transit time of those acoustic signals through the member, and after the acoustic signals have been transmitted through the material of known acoustic properties, determines the "material" transit time of the acoustic signals through the material. These time periods may be measured most simply by counting the number of clock pulses of known frequency emitted by the timer 43 between the time of launching the pulse and the sensing of the received pulse at the A/D converter 42. The microprocessor 38 then makes a mathematical "time" comparison of the member transit time to the material transit time and then relates that mathematical time comparison to the physical properties and integrity of the member. The mathematical time comparison may be made by either determining a difference between the member transit time and the material transit time, or by determining a ratio between the member transit time and the material transit time.

As a second method of using the densitometer, it may also determine the physical properties and integrity of the member 32 by determining and comparing the absolute attenuation of the broadband frequency components of the acoustic signals through the member without reference to a material having known acoustic properties. Using this method, the comparison of velocity to a standard is not necessary and absolute transit time of the pulse need not be calculated since it is attenuation that is measured. In such a mode, it is preferable that the transmit transducer 21 transmits an acoustic signal which has a broad range of frequency components, such as a simple ultrasonic pulse. In any case, the acoustic signal should have at least one specific frequency component.

In this attenuation comparison mode, the microprocessor 38 is programmed so that after the receive transducer 21 receives the acoustic signals transmitted through the bone member 32, it determines the absolute attenuation through the member 32 of the frequency component spectrum of the acoustic signals. It is to facilitate the measurement of attenuation that the excitation amplifier circuit 55 and the receiver amplifier 59 have amplification levels which may be digitally controlled. By successively varying the gain of the amplifiers 55 and 59 on successive pulses, the circuit of FIG. 4 can determine what level of gain is necessary to place the peak of the received waveform at a proper voltage level. This gain is, of course, a function of the level of attenuation of the acoustic pulse during transit through the member 32. After the receive transducer 21 receives acoustic signals, microprocessor 38 in conjunction with the signal processor 41 determines the absolute attenuation of individual specific frequency components of the received acoustic signal transmitted through the material. The digital signal processor 41 then makes mathematical "attenuation" comparisons of the corresponding individual specific frequency components through the member. A set of mathematical attenuation comparisons between corresponding frequency components may be thereby obtained, one comparison for each frequency component compared. The manner in which the attenuation functions with respect to frequency can thus be derived. The microprocessor 38 and digital signal processor 41 then relate that function to the physical properties and integrity of the member.

Figure 7:
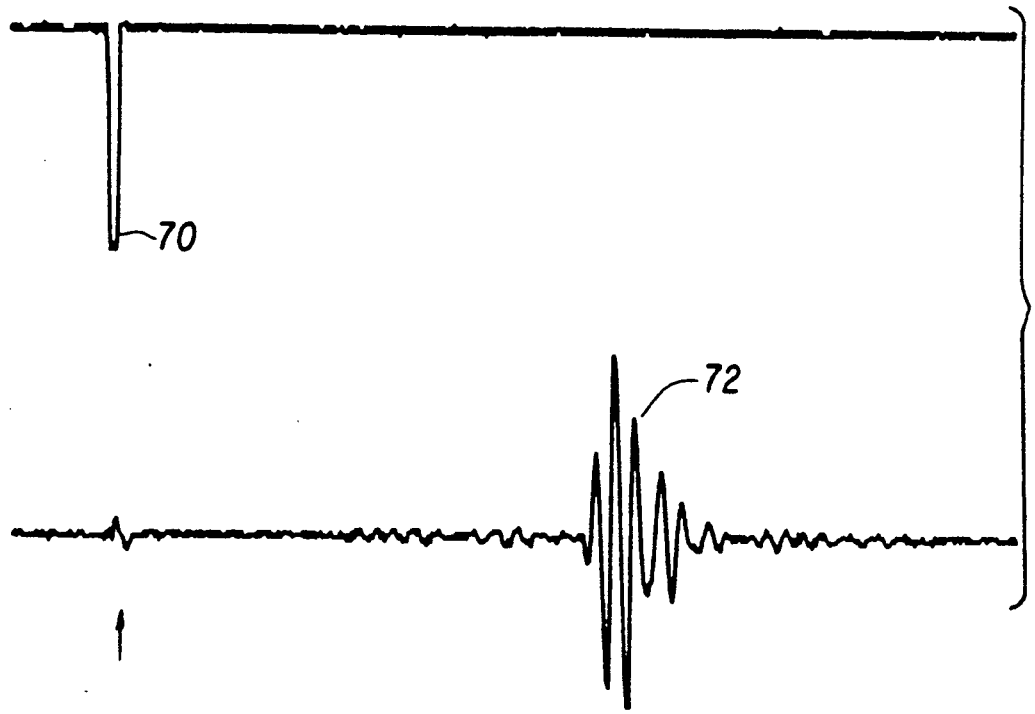
FIG. 7 is a sample of an actual ultrasonic pulse and response from an ultrasonic densitometer according to the present invention.
Figure 8:
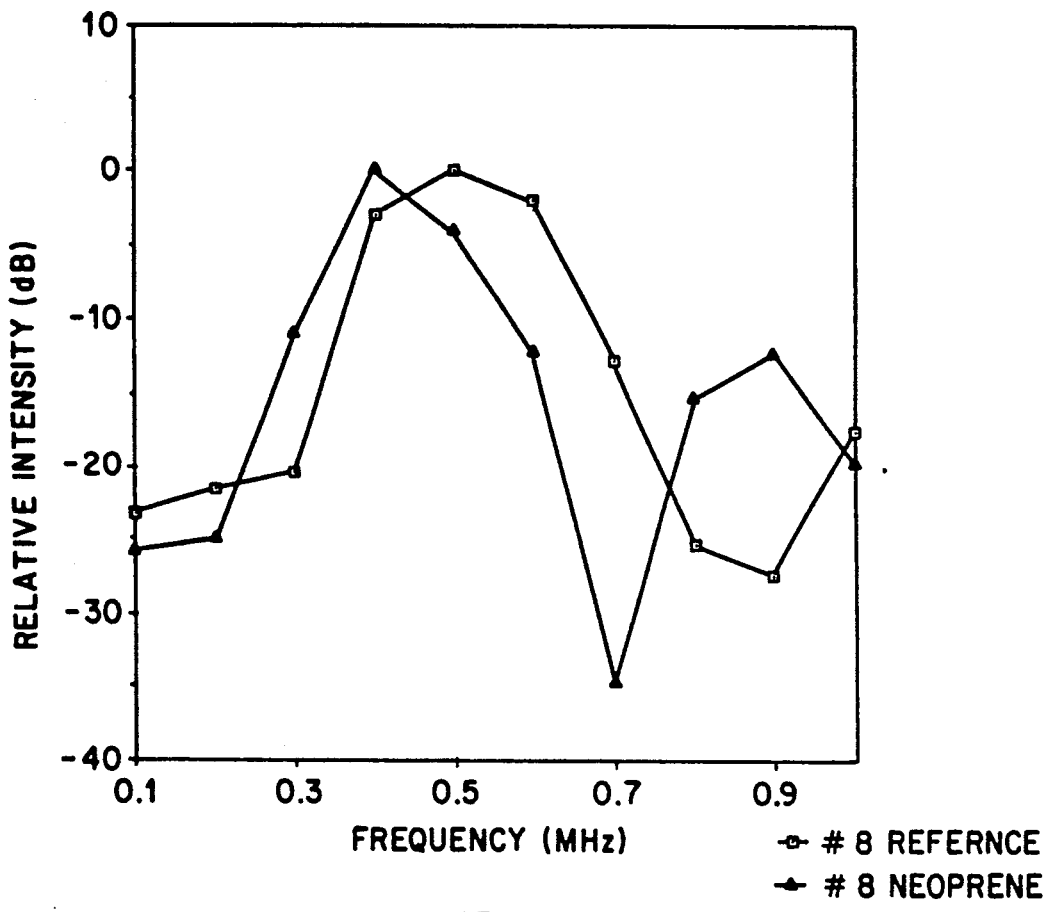
FIG. 8 is a sample plot of relative ultrasound pulse intensity over frequency range.
Figure 9:
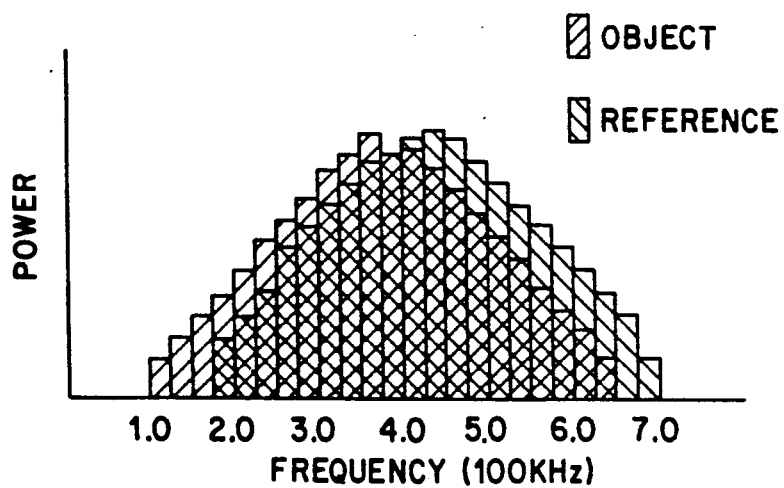
FIG. 9 is a graph in frequency domain illustrating the shift in alternation versus frequency characteristic of a measured object as compared to reference.

Shown in FIG. 7 is a sample broadband ultrasonic pulse and a typical received waveform. To achieve an ultrasonic signal that is very broad in the frequency domain, i.e., a broadband transmitted signal, an electronic pulse such as indicated at 70 is applied to the selected ultrasonic transducer in the transmit array 21 which then resonates with a broadband ultrasonic emission. The received signal, such as indicated at 72 in FIG. 7 in a time domain signal plot, is then processed by discrete Fourier transform analysis so that it is converted to the frequency domain. Shown in FIG. 8 is a pair of plots of sample received signals, in frequency domain plots, showing the shift in received signal intensity as a function of frequency between a reference object and a plug of neoprene placed in the instrument. FIG. 9 illustrates a similar comparison, with FIG. 8 using relative attenuation in the vertical dimension and FIG. 9 using absolute power of the received signal. Both representations illustrate the difference in relative intensities as a function of frequency illustrating how broadband ultrasonic attenuation varies from object to object. The actual value calculated, broadband ultrasonic attenuation, is calculated by first comparing the received signal against the reference signal, then performing the discrete Fourier transform to convert to frequency domain, then performing a linear regression of the difference in attenuation slope to derive broadband ultrasonic attenuation.

The mathematics of the discrete Fourier transform are such that another parameter related to bone member density may be calculated in addition to, or in substitution for, attenuation. When the discrete Fourier transform is performed of the time-domain signal, the solution for each point includes a real member component and an imaginary member component. The values graphed in FIGS. 8 and 9 are the amplitude of the received pulse as determined from this discrete Fourier transform by taking the square root of the sum of the squares of the real component and the imaginary component. The phase angle of the change in phase of the ultrasonic pulse as it passed through the member can be calculated by taking the arctangent of the ratio of the imaginary to the real components. This phase angle value is also calculated to bone member density.

The microprocessor 38 may also be programmed so that the densitometer simultaneously performs both functions, i.e. determines both transit time and absolute attenuation of the transmitted acoustic signals, first through the member and then through the material with known acoustic properties. The densitometer may then both derive the broadband ultrasonic attenuation function and make a mathematical time comparison of the member transit time to the material transit time. The microprocessor 38 and digital signal processor 41 then relate both the time comparison along with the attenuation function to the physical properties and integrity, or density of the member 32.

In yet another possible mode of operation the microprocessor 38 may be programmed so that the densitometer 10 operates in a mode whereby the need for calculating either the relative transit time or the attenuation of the acoustic signals through a material of known acoustic properties is eliminated. In order to operate in such a mode, the microprocessor 38 would include a database of normal absolute transit times which are based upon such factors as the age, height, weight, race or the sex of the individual being tested as well as the distance between the transducers or the thickness or size of the member. This database of normal transit times can be stored in the non-volatile memory or could be stored in other media. When testing an individual in this mode, the relevant factors for the individual are placed into the microprocessor 38 to select the pertinent normal transit time based on those factors. The transducers 21 are placed on the bone member being tested as described above. When the actuator button 12 is pressed, the acoustic signals are transmitted through the member 32. The receive transducer 21 receives those signals after they have been transmitted through the member, and the electronics 31 then determine the "member" transit time of the acoustic signals through the member. The microprocessor 38 and digital signal processor 41 then make a mathematical comparison of the measured member transit time to the selected database normal transit time, and relate the mathematical time comparison to the physical properties and integrity, to density of the member, which is displayed.

As an alternative output of the densitometer of the present invention, the digital display 18 could also include a display corresponding to the pattern of the array of elements on the face of the transducer 21 as seen in FIG. 3. This display could then display, for each element a through 1, a gray scale image proportional to the parameter, i.e. transit time or attenuation, being measured. This image may provide a visual indication to an experienced clinician as to the physical properties of the member presenting the patient.

Figure 6:
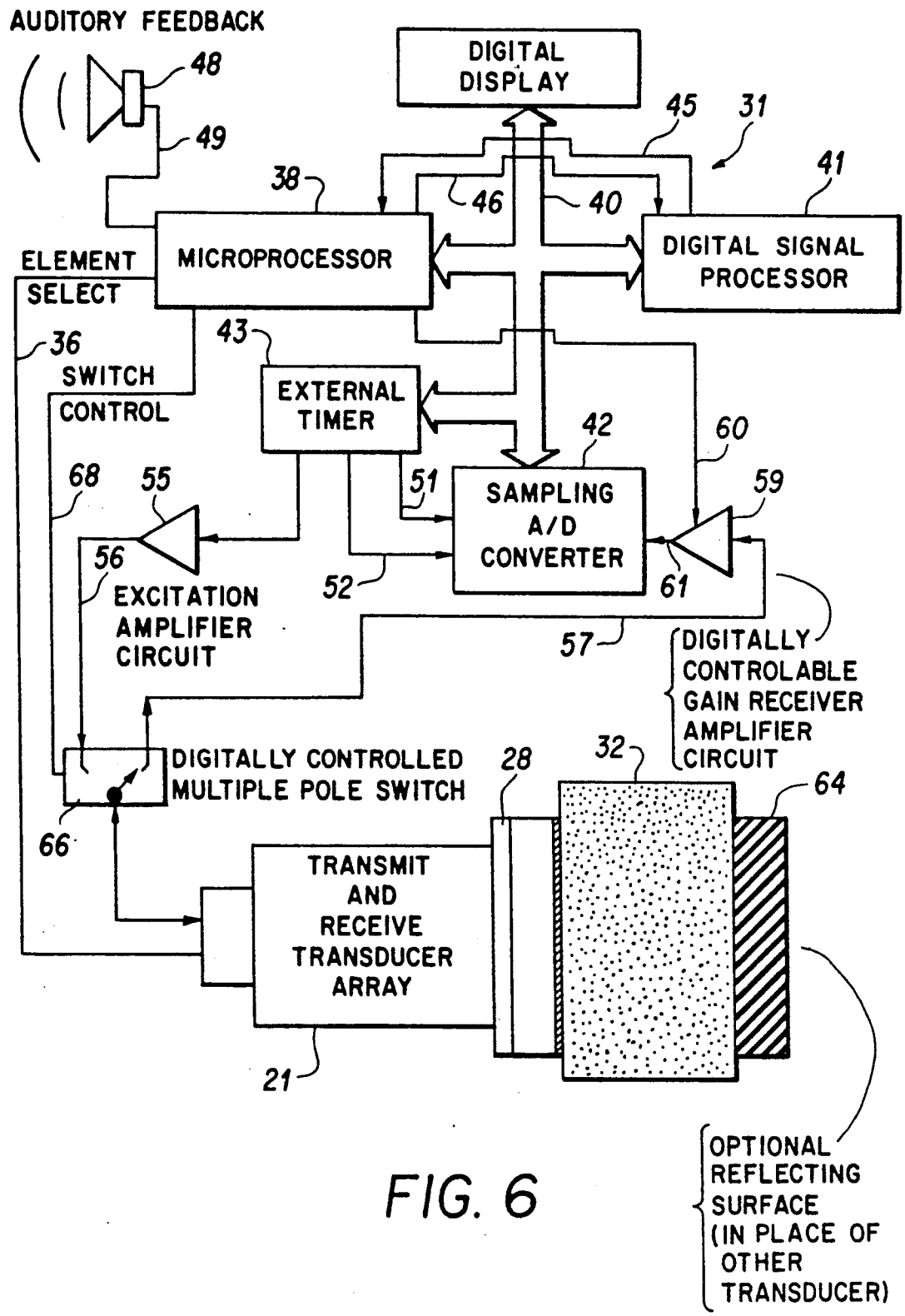
FIG. 6 is a schematic block diagram view of the circuitry of an alternative embodiment of an ultrasound densitometer constructed in accordance with the present invention.

Shown in FIG. 6 is a circuit schematic for an alternative embodiment of a ultrasonic densitometer constructed in accordance with the present invention. In the circuit of FIG. 6, parts having similar structure and function to their corresponding parts in FIG. 4 area indicated with similar reference numerals.

The embodiment of FIG. 6 is intended to function with only a single transducer array 21 which functions both as the transmit and receive transducer array. An optional reflecting surface 64 may be placed on the opposite side of the member 32 from the transducer array 21. A digitally controlled multiple pole switch 66, preferably an electronic switch rather than a physical one, connects the input to an output from the elements of the transducer array 21 selectively either to the excitation amplifier 55 or to the controllable gain receiver-/amplifier circuit 59. The switch 766 is connected by a switch control line 68 to an output of the microprocessor 38.

In the operation of the circuit of FIG. 6, it functions in most respects like the circuit of FIG. 4, so only the differences need be discussed. During the launching of an ultrasonic pulse, the microprocessor 38 causes a signal to appear on the switch control line 768 to cause the switch 66 to connect the output of the excitation amplifier 55 to the selected element in the transducer array 21. Following completion of the launching of the pulse, the microprocessor 38 changes the signal on the-istic control line 68 to operate the switch 66 to connect the selected element or elements as an input to the amplifier 59. Meanwhile, the pulse propagates through the member 32. As the pulse transits through the member, reflective pulses will be generated as the pulse crosses interfaces of differing materials in the member and, in particular, as the pulse exits the member into the air at the opposite side of the member. If the transition for the member to air does not produce a sufficient reflective pulse, the reflecting surface 64 can be placed against the opposite side of the member to provide an enhanced reflected pulse.

The embodiment of FIG. 76 can thus be used to analyze the physical properties and integrity of a member using only one transducer 21. All of the methods described above for such measurements may be used equally effectively with this version of the device. The transit time of the pulse through the member can be measured simply by measuring the time period until receipt of the reflected pulse, and then simply dividing by two. This time period can be compared to the transit time, over a similar distance, through a standard medium such as water. The time period for receipt of the reflected pulse could also be simply compared to standard values for age, sex, etc. Attenuation measurements to detect differential frequency measurement can be directly made on the reflected pulse. If no reflecting surface 64 is used, and is desired to determine absolute transit time, the thickness of the member or sample can be measured.

The use of the multi-element ultrasonic transducer array for the transducers 21, as illustrated in FIG. 3, enables another advantageous feature of the instrument of FIGS. 1-9. Using prior art densitometers it was often necessary to precisely position the instrument relative to the body member of the patient being measured to have useful results. The difficulty arises because of heterogeneities in the bone mass and structure of actual body members. A measurement taken at one location of density may be significantly different from a measurement taken close by. Therefore prior art instruments fixed the body member precisely so that the measurement could be taken at the precise location each time.

The use of the ultrasonic transducer array obviates the need for this precise positioning. Using the instrument of FIGS. 1-9, the instrument performs a pulse and response, performs the discrete Fourier transform, and generates a value for bone ultrasonic attenuation for each pair of transducer elements a through l. Then the microprocessor 38 analyses he resulting array of bone ultrasonic density measurements to reproducibly identify the same region of interest each time. In other words, since the physical array of transducers is large enough to reliably cover at least the one common region of interest each time, the measurement is localized at the same locus each time by electrically selecting the proper location for the measurement from among the locations measured by the array. The instrument of FIG. 1-9 is conveniently used by measuring the density of the os calcis as measured through eh heel of a human patient. When used in tis location, it has been found that a region of interest in the os calcis can be located reliably and repeatedly based on the comparisons of bone ultrasonic attenuation at the points in the array. The region of interest in the os calcis is identified as a local or relative minimum bone ultrasonic attenuation and/or velocity closely adjacent the region of highest attenuation values in the body member. Thus repetitive measurements of the bone ultrasonic attenuation value at this same region of interest can be reproducibly taken even through the densitometer instrument 10 is only generally positioned at the same location for each successive measurement.

This technique of using a multiple element array to avoid position cricicality is applicable to other techniques other than the determination of broadband ultrasonic attenuation as described here. the concept of using an array in comparing the array of results to determine measurement locus would be equally applicable to measurements taken of member-density based on a speed of sound transit time, other measurements of attenuation or on the calculation of phase angle discussed above. The use of such a multiple-element array, with automated selection of one element in the region of interest, can also by applied to other measurement techniques useful for generating parameters related to be one member density, such as measuring speed changes in the transmitted pulse such as suggested in U.S. Pat. No. 4,361,154 to Pratt, or measuring the frequency of a "sing-around" self-triggering pulse as suggested in ZU.S. Pat. No. 3,847,141 to Hoop. The concept which permits the position independence feature is that of an array of measurements generating an array of data points from which a region of interest is selected by a reproducible criterion or several criteria. The number of elements in the array also clearly can be varied with a larger number of elements resulting in a greater accuracy in identify in the same region of interest.

In this way, the ultrasound densitometer of the present invention provides a device capable of rapid and efficient determination of the physical properties of a member in vivo without the use of radiation. Because the densitometer is constructed to operate under the control of the microprocessor 38, it can be programmed to operate in one of several modes, as discussed above. This allows both for flexibility to clinical goals as well as efficient use of the device.

Figure 10:
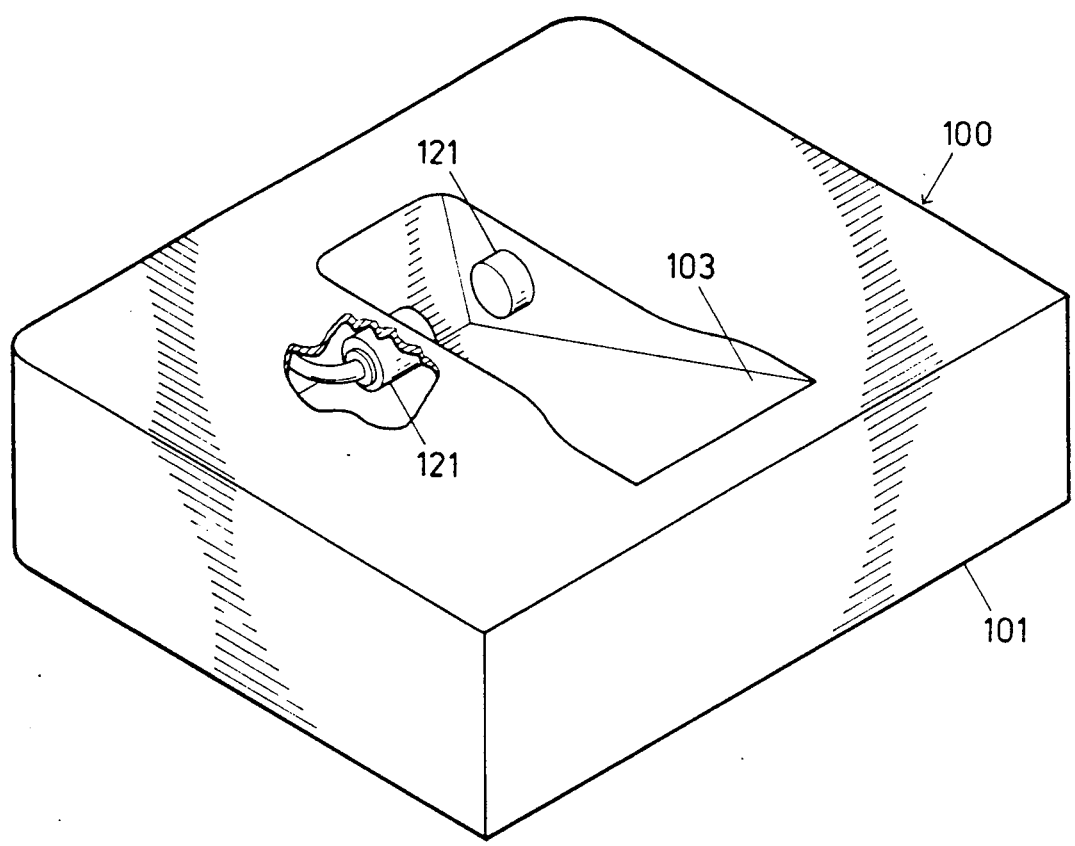
FIG. 10 is a perspective view of an alterative embodiment of the present invention.

Shown in FIG. 10 is another variation on an ultrasonic densitometer constructed in accordance with the present invention. In the densitometer 100 of FIG. 10, there are two ultrasonic transducer arrays 121, which are generally similar to the ultrasonic transducer arrays 21 of the embodiment of FIG. 1, except that the transducer arrays 21 are fixed imposition other than movable. The densitometer 100 includes a relatively large mounting case 101, which in this embodiment is rectangular, irf the top of which is formed a depression or basin 103. The as in 103 is elongated and has a generally triangular cross-sectional shape sized so as to receive a human foot therein. The transducer arrays 121 are positioned in the case 101 so that they extend into the base in 103 to be on the opposite sides of the heel of a foot placed in the basin 103. The general arrangement of the electrical components of FIG. 4 is unchanged in the ultrasonic densitometer 100 of FIG. 10, except that because the transducer arrays 12 are fixed, they do not contact the opposite sides of the heel of the patient but instead are located spaced away from it.

In the operation of the ultrasonic densitometer 100 of FIG. 10, the basin 103 is filled with water. The patient places his or her foot in the basin 103 with their sole resting on the bottom and their heel resting against the back of the basin 103. The intent is to position the transducer arrays 121 on either side of the os calcis. For the average adult population, i has been demonstrated that placing the transducers approximately 4 cm up from the sole and 3.5 cm forwardly from the rearward edge of the heel places the transducers in the desired region and focused on the os calcis.

The principle of operation of the ultrasonic densitometer of FIG. 10 can be understood as similar to that of FIG. 1, except that the order of pulsing and measurement can be varied. In the apparatus of FIG. 1, the measurement pulse through the member was generally performed before the reference pulse through the homogeneous standard, i.e. water. In the densitometer 100 of FIG. 10, since the distance between the transducers is fixed, the reference pulse through the homogeneous standard material, which is simply the water in the basin 103, may be conducted either before or after measurement pulse through a live member is performed. In fact, if the temperature of the water in the basin 103 is held steady by a temperature control mechanism, the standard transit time measurement can be simply made once for the instrument and thereafter only measurement pulses need be transmitted. The transit times of the measurement pulses then may be correlated to the standard reference transit time through the water to gi e an indication of the integrity of the member just measured.

Through empirical experimentation with the densitometer of FIG. 10, it has been determined that it is also possible, if desired, to dispense with the reference pulse entirely. This may be done by determining a standard transit time value, or, since the distance between the transducers is fixed, a standard transit velocity. By empirical testing it has been determined that by proper selection of such a standard value, and by holding the water in the basin within a temperature range, no reference pulse need be launched or measured.

Using this variation, a mathematical relation of the measured transit time, or transit velocity, must be made to the standard. Since, in the interests of accuracy, it is preferred to use both charges in transit time (velocity) and charges in attenuation to evaluate a member in vivo; the following formula has been developed to provide a numerical value indicative of the integrity and mineral density of a bone:

$$\text{bone integrity value} = (SOS - T)^2 \times (BUA/1000)$$

In this formula, "SOS" indicates the speed of sound, or velocity, of the measurement ultrasonic pulse through the member, and is expressed in meters per second. The speed of sound (SOS) value is calculated from the measured transit time by dividing a standard value for the member width by the actual transit time measured. For an adult human heel, it has been found that assuming a standard human heel width of 40 mm at the point of measurement results in such sufficient and reproducible accuracy that actual measurement of the actual individual heel is not needed.

In the above formula, "T" represents a standard minimum value. Two alternative values are possible. One alternative is to set T to the speed of sound value for water, i.e. the reference pulse velocity. This value is about 1500 m/sec for water at 28° C. The principal drawback to this approach is that it has been found, surprisingly, that some people actually have a density value in their heel that is below that of water. For such persons, using the standard water velocity would make the bone integrity value a negative number. Therefore, another alternative is to use the lowest measured human value as T, which in the experience of the investigators here to date is 1475 m/sec.

Lastly in the above formula, BUA is broadband ultrasonic attenuation, as described in greater detail above. The division of 1000 merely scales the influence of the BUA measurement relative to the SOS measurement, which has been determined to be a more effective predictor of bone density.

Measured values of SOS range between 1475 and 1650 m/sec. Measured values of BUA range between 30 and 100 dB/MHz. Using a T=1475, these ranges yield values ranging from very small, i.e. 18, up to relatively large, i.e. around 3000. Thus the bone integrity values thus obtained exhibit a wide range and are readily comprehensible. It has been determined, again by clinical testing, that persons with a bone integrity value of less than 200 have low spinal bone mineral density, that those in the range of 200-400 have marginal spinal bone mineral density, and that those having bone integrity values of over 400 have acceptable and high levels of spinal bone mineral density.

To verify the accuracy of this approach in predicting spinal bone density, patients were tested using the apparatus of FIG. 10 and also with a dual photon absorptiometry densitometer of accepted standard design. The results of using the ultrasonic densitometer of FIG. 10 have demonstrated that the speed of sound measurement made using this device had a correlation in excess of 0.95 with the measured values of spinal bone density, indicating very good consistency with accepted techniques. However, an occasional patient was tested who exhibited an SOS value in the normal range, but who exhibited a BUA value indicating very poor bone integrity. Accordingly the bone integrity value was developed to accommodate such deviant results. The value is weighted toward SOS, since that is the principaly used reliable predictor value, with a secondary factor including BUA to include such individuals. In fact, the power of the SOS factor may also be increased to the third or fourth power, as opposed to merely the second power, to increase the importance of the SOS term. Since this method utilizing ultrasonic measurement of the heel is quick and free from radiation, it offers a promising alternative for evaluation of bone integrity.

The densitometer 100 may be used with or without an array of ultrasonic transducers in the transducers 121. In its simplest form the mechanical alignment of the heel in the device can be provided by the shape and size of the basin 103. While the use of an array, and region-of-interest scanning as described above, is most helpful in ensuring a reproducible and accurate measurement, mechanical placement may be acceptable for clinical utility, in which case only single transducer elements are required.

It is specifically intended that the present invention mot be specifically limited to the embodiments and illustrations contained herein, but embraces all such modified forms thereof as come within the scope of the following claims.

We claim:

1. A method for measuring the physical properties and integrity of a member in vivo comprising the steps of:
   (a) providing a pair of spaced ultrasonic transducers;
   (b) launching at least two acoustic signals between the transducers, one of the signals being through at least the member and the other of the signals being through a standard inanimate homogeneous material of known acoustic properties, the distance between the two transducers remaining fixed for the two signal launches;
   (c) determining the transit time for each of the two acoustic signals between the two transducers;
   (d) making a mathematical time comparison between the transit time of the signal through the member with the transit time of the signal through the standard material; and
   (e) relating the mathematical time comparison to the physical properties of the member.

2. A method as claimed in claim 1 wherein the acoustic signal launched through the reference is launched before the acoustic signal launched through the member.

3. A method as claimed in claim 1 wherein the distance between the transducers is fixed and wherein the measurement of the transit time through the reference is made once and then the same measurement is used for comparison with a plurality of signals launched through different members.

4. A method for measuring the physical properties and integrity of a member in vivo comprising the steps of:
   (a) providing a pair of spaced ultrasonic transducers with fixed physical distance between them surrounding a receptacle sized and shaped to receive a body member therein;
   (b) placing a body member in the receptacle;
   (c) launching an ultrasonic pulse of known amplitude from one transducer to the other;
   (d) determining the transit time of the ultrasonic pulse from one transducer to the other;
   (e) determining the broadband ultrasonic attenuation from one transducer to the other;
   (f) calculating a value related to bear integrity using the formula value=(transit time from step (d)$-$T$)^2 \times$(attenuation from step (e)/K); where T is a standard minimum time value and K is a constant; and
   (g) providing as an output the value thus calculated.

5. A method as claimed in claim 4 wherein the receptacle is sized and shaped to receive a human heel therein.

6. A method as claimed in claim 4 wherein the time value from step (d) and the value T are each divided by a standard distance value to convert them to velocity values.

7. A method as claimed in claim 6 wherein the standard distance value represents the width of a human heel.

8. A method as claimed in claim 4 wherein the standard minimum time value T is the value for the transit time of an ultrasonic pulse through water.

9. A method as claimed in claim 4 wherein the standard minimum time value T is a value selected to approximate the transit time of an ultrasonic pulse through an exceptionally low density human patient.

10. A method as claimed in claim 4 wherein the value K is 1000.

* * * * *